(12) United States Patent
Demoute et al.

(10) Patent No.: US 6,498,267 B2
(45) Date of Patent: Dec. 24, 2002

(54) 5-HALO-4-FLUORO-4,7,7-TRIMETHYL-3-OXABICYCLO[4.1.0]HEPTAN-2-ONES, PROCESS FOR THEIR PREPARATION AND THEIR USE FOR PREPARING CYCLOPROPANECARBOXYLIC ACIDS

(75) Inventors: Jean Pierre Demoute, Kelkheim (DE); Günter Hömberger, Kelkheim (DE); Sergej Pazenok, Kelkheim (DE); Didier Babin, Montigny (FR)

(73) Assignee: Aventis CropScience GmbH, Frankfurt (DE)

( * ) Notice: Subject to any disclaimer, the term of this patent is extended or adjusted under 35 U.S.C. 154(b) by 0 days.

(21) Appl. No.: 09/981,427

(22) Filed: Oct. 17, 2001

(65) Prior Publication Data
US 2002/0045766 A1 Apr. 18, 2002

Related U.S. Application Data

(62) Division of application No. 09/709,102, filed on Nov. 8, 2000, now Pat. No. 6,337,407.

(30) Foreign Application Priority Data
Nov. 10, 1999 (DE) .......................... 199 54 160

(51) Int. Cl.$^7$ ............................................. C07C 69/743
(52) U.S. Cl. ........................................................ 560/124
(58) Field of Search ................................ 560/124, 129, 560/130

(56) References Cited

U.S. PATENT DOCUMENTS

| | | | | |
|---|---|---|---|---|
| 4,279,835 A | * | 7/1981 | Martel et al. | ................ 260/465 |
| 4,463,014 A | * | 7/1984 | Martel et al. | ................ 424/275 |
| 4,513,147 A | * | 4/1985 | Martel et al. | ................ 562/506 |

FOREIGN PATENT DOCUMENTS

WO     WO 99/32426    * 7/1999

* cited by examiner

*Primary Examiner*—Joseph K. McKane
*Assistant Examiner*—Golam M M Shameem
(74) *Attorney, Agent, or Firm*—Frommer Lawrence & Haug LLP

(57) ABSTRACT

5-Halo-4-fluoro-4,7,7-trimethyl-3-oxabicyclo[4.1.0]heptan-2-ones, process for their preparation and their use for preparing cyclopropanecarboxylic acids Compounds of the formula (I),

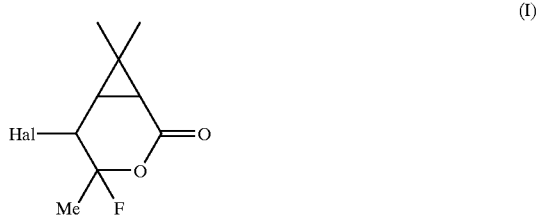

in which Hal is Cl, Br or I, are suitable for use as intermediates in the preparation of pyrethroids.

3 Claims, No Drawings

5-HALO-4-FLUORO-4,7,7-TRIMETHYL-3-OXABICYCLO[4.1.0]HEPTAN-2-ONES, PROCESS FOR THEIR PREPARATION AND THEIR USE FOR PREPARING CYCLOPROPANECARBOXYLIC ACIDS

This application is a divisional of U.S. application Ser. No. 09/709,102, filed Nov. 8, 2000, allow on Jul. 17,2001, U.S. Pat. No. 6,337,407.

DESCRIPTION

5-Halo-4-fluoro4,7,7-trimethyl-3-oxabicyclo[4.1.0]heptan-2-ones, process for their preparation and their use for preparing cyclopropanecarboxylic acids Pyrethroids are an important class of insecticides whose activity is based on a strong action on the sodium channels in the nerve membranes of insects.

WO-A 99/32426 describes derivatives of 2,2-dimethyl-3-(2-fluorovinyl)cyclopropanecarboxylic acid as highly active pyrethroids. The preparation of this acid is carried out by multistep reductive transformation of 2,2-dimethyl-3-(2-fluoro-3-hydroxy-3-oxo-1-propenyl)cyclopropane-carboxylic acid esters.

It was an object of the present invention to provide novel advantageous synthesis routes for the acid and thus for the pyrethroids mentioned.

Surprisingly, it has now been found that 2,2-dimethyl-3-(2-fluorovinyl)cyclopropanecarboxylic acid can be prepared in simple manner in high purity and good yields by halofluorination of 4,7,7-trimethyl-3-oxabicylo[4.1.0]hept-4-en-2-one to give the novel 5-halo-4-fluoro-4,7,7-trimethyl-3-oxabicyclo[4.1.0]heptan-2-ones, followed by reductive elimination.

Halofluorination of enollactones is known in principle (see M. Brand and S. Rozen, J. of Fluorine Chem. (1982), 20, 419 or Houben-Weyl, Methoden der organischen Chemie [Methods of organic chemistry], Vol. E 10).

However, halofluorination is limited to only those substrates which are stable under halofluorination conditions. Furthermore, it is known that cyclopropane or its derivatives react with HF or even with HF/Py even at room temperature with ring-opening and formation of fluoropropanes or cyclobutane derivatives (see, for example, J. Org. Chem. (1979), 44, 3873 or Tet. Lett. (1987), 28, 6313).

Bicyclic enollactones comprising three-membered rings are highly sensitive to acids, bases and oxidizing agents and usually react with opening of the lactone or cyclopropane ring. Because of this, it is surprising that the chloro-, bromo- or iodofluorination of enollactones gives chlorofluoro, bromofluoro or iodofluoro compounds in good yields and high purities.

The invention provides halogenated lactones of the formula (I),

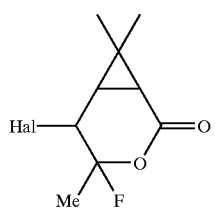

in which Hal is Cl, Br or I.

The compounds of the formula (I) embrace all possible stereoisomers.

Compounds of the formula (I) are highly suitable for use as intermediates in the preparation of pyrethroids, as described in WO-A 99/32426.

The compounds of the formula (I) are prepared by reacting an enollactone (II) with a halofluorinating agent ("HalF")

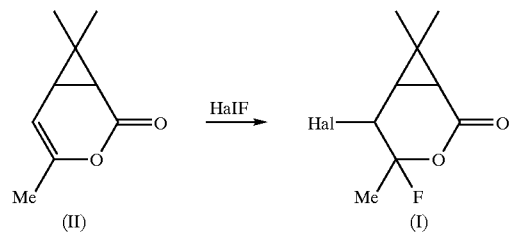

in which Hal is Cl, Br or I.

This process also forms part of the subject matter of the invention.

The term halofluorinating agent is to be understood as meaning reagents or combinations thereof capable of transferring positive halogen atoms and fluoride anions to organic compounds.

The reaction can be carried out with ClF, BrF (see, for example, M. Brand and S. Rozen, J. of Fluorine Chem. (1982), 20, 419) or preferably with an equivalent, comprising a compound which contains one or more positive halogen atoms (Hal+), and also hydrofluoric acid or salts thereof (see, for example, F. Camps et al., J. Org. Chem. (1989), 54,4294).

Preferred Hal$^+$ sources are N-chloroacetamide, hexachloromelamine, N-bromoacetamide, N-chlorosuccinimide (NCIS), N-bromosuccinimide (NBS), N-iodosuccinimide, 1-bromo-3,5,5-trimethylhydantoin, N,N-dibromo-5,5-dimethylhydantoin (DBH), and other halogenating agents are also possible. It is also possible to use a mixture of two or more halogen compounds. Particularly preferred halogenating agents are NBS and DBH, and very particular preference is given to DBH.

The fluorides used are, in general, fluorides of the formula (III):

$$\text{KAT } H_nF_{n+1} \tag{III}$$

in which KAT denotes a stoichiometric equivalent of an alkaline earth metal ion, an alkali metal ion, a tetraalkylammonium ion, a tetraalkylphosphonium ion, a tetraalkylphosphonium ion or a tetrakis(dialkylamino)phosphonium ion, where alkyl is an alkyl group with preferably 1 to 6 carbon atoms, alkyl is an alkyl group with 6 to 12 carbon atoms and n is 0, 1, 2, 3, 4 or 5.

Without the lists being known to be complete, the following fluorides may be mentioned:

Potassium hydrogen difluoride, potassium tetrahydrogen pentafluoride, tetramethylammonium fluoride, tetramethylammonium hydrogen difluoride, tetramethylammonium dihydrogen trifluoride, tetraethylammonium hydrogen difluoride, tetrabutylammonium hydrogen difluoride, tetrabutylammonium dihydrogen trifluoride, benzyltrimethylammonium hydrogen difluoride, tetraphenylphosphonium hydrogen difluoride, tetrakis(diethylamino)phosphonium hydrogen difluoride, HF, HF/pyridine complex, Et$_3$N×3HF, Bu$_3$N×3HF. It is also possible to use a mixture of two or more fluorides. It is furthermore possible to use systems of fluorine-containing compounds and water, for example SiF$_4$/

H$_2$O, SbF$_3$/H$_2$O, AlF$_3$/H$_2$O. It is furthermore possible to use [ClF] from Cl$_2$ and F$_2$ or [BrF] from Br$_2$ and F$_2$ (see, for example, M. Brand and S. Rozen, J. of Fluorine Chem. (1982), 20, 419).

The process can be carried out in the presence or absence of a solvent. If solvents are used, both polar and nonpolar solvents are suitable. Suitable solvents are, for example: hexane, cyclohexane, dioxane, diethyl ether, diisopropyl ether, toluene, dichloromethane, dichloroethane and polyethers.

The reaction temperature is usually between −30 and +30° C., preferably between −15 and +20° C., and depends, inter alia, on the type of the halofluorinating agent, in the manner known to the person skilled in the art.

The fluorides are generally employed in amounts of from 0.2 to 2, in particular from 0.25 to 1.5, preferably from 0.4 to 1 mol, based on 1 mol of enollactone. The amount of fluoride depends on the number of fluoride atoms in the molecule. Thus, the use of HF requires twice the amount, compared to tetrabutylammonium hydrogen difluoride. It has to be taken into account that there may be cases where an excess of fluoride may lead to undesirable side reactions. In these cases, it is recommended to use a substoichiometric amount of fluoride.

The halogenating agent is generally employed in an amount of from 0.5 to 2 mol, preferably from 0.4 to 1 mol, based on 1 mol of enollactone. The amount of halogenating agent. depends on the number of halogen atoms in the molecule. Thus, the use of N-bromosuccinimide requires twice the amount, compared to dibromohydantoin.

The enollactone of the formula (II) embraces all possible stereoisomeric forms. It is known and can be synthesized by methods known from the literature (see, for example, D. Bakshi et al., Tetrahedron (1989), 45, 767).

The halofluorination of enollactones of the formula (II) gives an isomer mixture of a plurality of stereoisomers; in the case of the bromofluorination of (1R,6S)-4,7,7-trimethyl-3oxabicyclo[4.1.1]hept-4-en-2-one, for example, an isomer mixture of mainly three stereoisomers is formed:

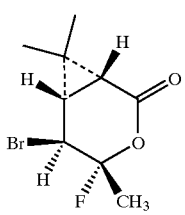

A

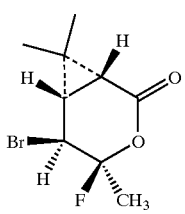

B

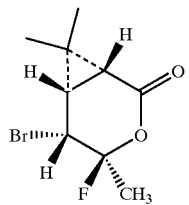

C

However, in a simple manner, known to the person skilled in the art, it is possible to influence the isomer ratios by reaction conditions (time, temperature etc.) (see Table 1 in the examples). Isomer A can be isolated in pure form by crystallization from alcohol. The other isomers can be isolated by chromatography, for example by medium pressure liquid chromatography (MPLC) using hexane/ethyl acetate mixtures.

The compounds of the formula (I) can be reacted further with a reducing agent to give cis-cyclopropanecarboxylic acids of the formula (IV):

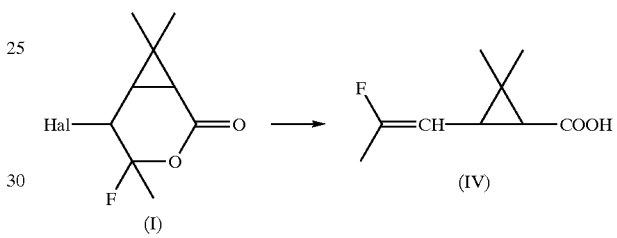

This process and a process for preparing cyclopropanecarboxylic acids of the formula (IV) by successive halofluorination and reduction of the enollactone (II) also form part of the subject matter of the invention.

Suitable reducing agents are all customary reducing agents, such as Mg, Fe, Zn, Sn, Al, Bu$_3$SnH, LiAlH$_4$ (see, for example, J. Am. Chem. Soc., 121, 4155, 1990). The cyclopropanecarboxylic acid of the formula (IV) can be formed as a mixture of two geometrical isomers.

The acid of the formula (IV) or a functional derivative of the acid can be converted with a compound of the formula (V),

R-X            (V)

in which X is a leaving group, preferably OH, Cl, Br, I, OTosyl (tosyl: p-toluenesulfonyl) or OMesyl (mesyl: methanesulfonyl), and R is the radical of an alcohol from the pyrethroid group into a compound of the formula (VI)

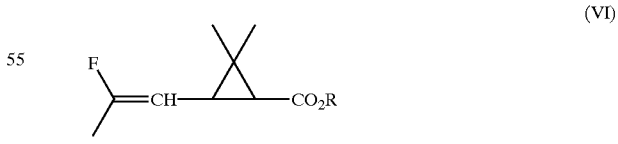

(VI)

in which R is as defined above.

Here, R preferably has the meanings mentioned in formula (I) in WO-A 99/32426. This publication is expressly incorporated herein by way of reference.

The esters of the formula (VI) can be obtained by esterification of corresponding carboxylic acids (or their reactive derivatives) with alcohols (or their reactive derivatives) by the DCC method (DCC=dicyclohexylcarbodiimide), or analogously to DE-A 44 27 198. The corresponding carboxylic acids and alcohols are known or can be prepared analogously to known processes.

Suitable reactive derivatives of the carboxylic acids mentioned are, in particular, the acyl halides, in particular the chlorides and bromides, further the anhydrides, for example also mixed anhydrides, azides or esters, in particular alkyl esters having 1–4 carbon atoms in the alkyl group.

Suitable reactive derivatives of alcohols are, in particular, the corresponding metal alkoxides, preferably those of an alkali metal, such as sodium or potassium.

The esterification is advantageously carried out in the presence of an inert solvent. Highly suitable are, in particular, ethers, such as diethyl ether, di-n-butyl ether, THF (tetrahydrofuran), dioxane or anisol, ketones, such as acetone, butanone or cyclohexanone, amides, such as DMF (NiN-dimethylformamide) or hexamethylphosphoramide, hydrocarbons, such as benzene, toluene or xylene, halogenated hydrocarbons, such as carbon tetrachloride, dichloromethane or tetrachloroethylene, and sulfoxides, such as dimethylsulfoxide or sulfolane.

Accordingly, the invention also provides a process for preparing a compound of the formula (VI),

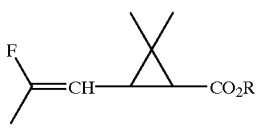
(VI)

in which R is the radical of an alcohol from the pyrethroid group, which comprises the following steps:
a) Reaction of an enollactone of the formula (II) with a halofluorinating agent to give a compound of the formula (I),
b) Reaction of the compound of the formula (I) with a reducing agent to give a cyclopropanecarboxylic acid of the formula (IV) and
c) Esterification of cyclopropanecarboxylic acid of the formula (VI) with a compound (V), $$R-X \quad (V)$$

in which X and R are as defined above.

Compounds of the formula (VI) which are preferably prepared by the process according to the invention are Examples 1 to 33 of WO-A 99/32426, which is expressly incorporated herein by way of reference.

The synthesis of the corresponding alcohol radicals is reported in WO-A 99/32426 and the literature cited therein.

The invention also provides the use of compounds of the formula (I) as intermediates in the preparation of pyrethroids, preferably those of the formula (VI).

The content of the German patent application 199 54 160.4, the priority of which is claimed by the present application, and of the enclosed abstract is expressly incorporated herein by way of reference.

The invention is illustrated in more detail by the examples, without being limited in any way.

EXAMPLES

Halofluorination (General Method)

In a three-necked flask fitted with bubble counter, thermometer, mechanical stirrer and dropping funnel, halogenating agent and fluoride were initially charged in a solvent under $N_2$, and the enollactone was added at a certain temperature. After the addition had ended, the solution was stirred for a certain additional amount of time, and the reaction was then terminated by addition of water and $Na_2SO_3$. The product was extracted with diethyl ether. The ether phase was washed with water, dried with $MgSO_4$, filtered and concentrated, and the residue was purified. According to this method, the following compounds were obtained:

Isomer A (1R,4R,5S,6S)-5-bromo-4-fluoro-4,7,7-trimethyl-3-oxabicyclo[4.1.0]heptan-2-one M.p. 94° C.
$^1$H-NMR (CDCl$_3$, 300 MHz): 1.23(s, 3H, CH$_3$); 1.3(s, 3H, CH$_3$); 1.8(m, 2H); 1.90(d, $^3$J=19.5 Hz, 3H, CH$_3$,); 4.0(d.d, J=9; 3 Hz, 1H) ppm $^{19}$F NMR (CDCl$_3$, 300 MHz): −100.7(d.qw) ppm Isomer B
(1R,4S,5S,6S)-5-bromo-4-fluoro-4,7,7-trimethyl-3-oxabicyclo[4.1.0]heptan-2-one $^1$H-NMR (CDCl$_3$, 300 MHz): 1.30(s, 3H, CH$_3$); 1.4(s, 3H, CH$_3$); 1.84(d, $^3$J=19 Hz, 3H, CH$_3$); 1.94(m, 2H); 4.8(m, 1H) ppm $^{19}$F NMR (CDCl$_3$, 300 MHz): −79.7(d.qw, J38.2; 19 Hz) ppm Isomer C
1R,4S,5R,6S)-5-bromo-4-fluoro-4,7,7-trimethyl-3-oxabicyclo[4.1.0]heptan-2-one $^{19}$F NMR (CDCl$_3$, 300 MHz): −138.7(d.qw, J38.2; 19 Hz) ppm

TABLE 1

Halofluorination of enollactone

| Ex. No. | Enollactone (mol) | Hal$^+$ (mol) | F$^−$ (mol) | Solvent | T° C., (time, h) | Yield$^+$ (%) |
|---|---|---|---|---|---|---|
| 1 | 1 | NCS (1.5) | Me$_4$N HF$_2$ (0.9) | CH$_2$Cl$_2$ | −10 (15) | 38 |
| 2 | 1 | NBS (1.8) | Me$_4$N H$_2$F$_3$ (1) | CH$_2$Cl$_2$ | −15 (20) | 42 |
| 3 | 1 | DBH (1) | Et$_4$N H$_2$F$_3$ (0.8) | DICIE | −15 (15) | 48 |
| 4 | 1 | DBH (1) | Bu$_4$N H$_2$F$_3$ (0.85) | Toluene | 0 (12) | 65 |
| 5 | 1 | NBS (1.8) | Bu$_4$N H$_2$F$_3$ (1.2) | DIPE | 0 | 56 |
| 6 | 1 | DBH (0.85) | Bu$_4$N H$_2$F$_3$ 0.8 | Dioxane | 20 (15) | 45 (isomer A) 20 (isomer B) |
| 7 | 1 | DBH (0.85) | Bu$_4$N H$_2$F$_3$ 0.8 | Dioxane | 10 (15) | 49 (isomer A) 14 (isomer B) |
| 8 | 1 | DBH (0.8) | Bu$_4$N H$_2$F$_3$ 0.8 | Dioxane CH$_2$Cl$_2$ | 0 (15) | 55 (isomer A) 8 (isomer B) |
| 9 | 1 | DBH (0.8) | Bu$_4$N H$_2$F$_3$ (0.5) | Dioxane | 0–10 | 38 |
| 10 | 1 | DBH (1) | HF/Py (1) | CH$_2$Cl$_2$ | 10 (12) | 51 |
| 11 | 1 | DBH (1) | KH$_4$F$_5$ (0.5) | CH$_2$Cl$_2$ | −15 (12) | 47 |

*Yield of the isomer mixture.

NCS=N-chlorosuccinimide
NBS=N-bromosuccinimide
DIPE=Diisopropyl ether
DICIE=Dichloroethane
DBH=N,N-Dibromo-5,5-dimethylhydantoin
Py=Pyridine

EXAMPLE 12

(1R-cis)-3-[(E)-2-Fluoropropenyl]-2,2-dimethylcyclopropanecarboxylic acid and (1R,cis)-3-[(Z)-2-fluoropropenyl]-2,2-dimethylcyclopropanecarboxylic acid.

In a three-necked flask fitted with bubble counter, thermometer and mechanical stirrer, 25.2 g (0.1 mol) of an isomer mixture of 5-bromo-4-fluoro-4,7,7-trimethyl-7-fluoro-3-oxabicyclo[4.1.0]heptan-2-one and 150 ml of acetic acid were initially charged, and 12.6 g (0.2 mol) of zinc dust were added a little at a time over a period of 1 h. After the addition had ended, the solution was stirred for another 4 h, the remaining Zn was filtered off and the solution was admixed with 200 ml of ice water. The product was extracted with diethyl ether. The etherol phase was washed with water, dried (MgSO$_4$), filtered and concentrated. The acids were isolated by chromatography. Yield 21%, oil.

(1R-cis)-3-[(E)-2-Fluoropropenyl]-2,2-dimethylcyclopropanecarboxylic acid $^1$H-NMR (CDCl$_3$, 300 MHz): 1.22(d, 6H); 1.7 (t, 2H); 1.92(d, 3H); 5.4(dd, 1 H) ppm $^{19}$F NMR (CDCl$_3$, 300 MHz): −93.3(d.qw, J=21; 19 Hz) ppm 1R-cis)-3-[(Z)-2-Fluoropropenyl]-2,2-dimethylcyclopropanecarboxylic acid $^1$H-NMR (CDCl$_3$, 300 MHz): 1.24(d, 6H); 1.7(m,1H); 1.96(d, 3H); 2.2(m, 1H); 4.86(dd, 1H) $^{19}$F NMR (CDCl$_3$, 300 MHz): −103.7(d.qw, J=39; 18 Hz) ppm

What is claimed is:

1. A process for preparing a compound of the formula (VI)

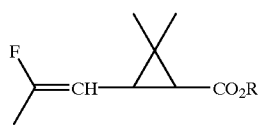

(VI)

in which R is the radical of an alcohol from the pyrethroid group, which comprises the following steps:

a) reaction of an enollactone of the formula (II)

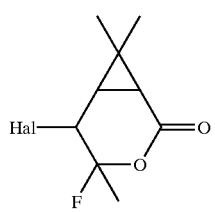

(II)

with a halofluorinating agent to give a compound of the formula (I)

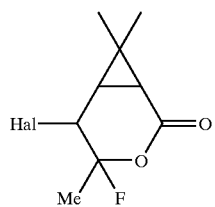

(I)

b) reaction of the compound of the formula (I) with a reducing agent to give a cyclopropanecarboxylic acid of the formula (IV)

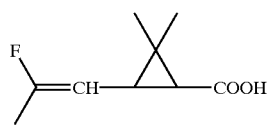

(IV)

and c) esterification of cyclopropanecarboxylic acid of the formula (IV) with a compound (V)

R–X     (V)

in which X is a leaving group and R is the radical of an alcohol from the pyrethroid group.

2. The process as claimed in claim 1, wherein Hal in formula (I) is Br.

3. The process for preparing a compound of the formula (I) as claimed in claim 1, which comprises reacting an enollactone of the formula (II) with a halo fluorinating agent ("HalF")

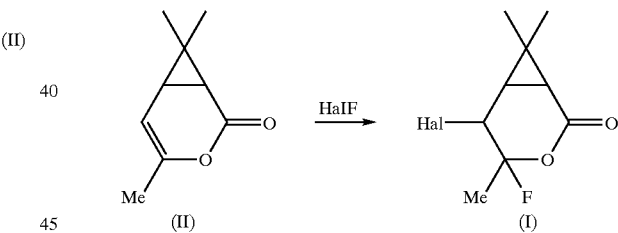

in which Hal is Cl, Br or I.

* * * * *